US00PP34610P3

(12) United States Plant Patent
Olesen

(10) Patent No.: US PP34,610 P3
(45) Date of Patent: Sep. 27, 2022

(54) MINIATURE ROSE PLANT NAMED 'POULPAH106'

(50) Latin Name: *Rosa hybrida*
Varietal Denomination: Poulpah106

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 1 day.

(21) Appl. No.: 17/300,612

(22) Filed: Sep. 7, 2021

(65) Prior Publication Data

US 2022/0095502 P1 Mar. 24, 2022

(30) Foreign Application Priority Data

Sep. 21, 2020 (QZ) ..... PBR 2020/2249

(51) Int. Cl.
*A01H 5/02* (2018.01)
*A01H 6/74* (2018.01)

(52) U.S. Cl.
USPC ..... Plt./122
CPC ..... *A01H 6/749* (2018.05)

(58) Field of Classification Search
USPC ..... Plt./122, 129
CPC ..... A01H 5/0222
See application file for complete search history.

(56) References Cited

PUBLICATIONS https://www.poulsenroser.dk/en/roses/ShowProduct/55509?productGroup=PAH; Oct. 8, 2021; 2 pages.*
https://www.kordes.us/plants/hella: Oct. 8, 2021; 1 page.*

* cited by examiner

*Primary Examiner* — Kent L Bell

(57) ABSTRACT

A new garden rose plant of the Miniature class which has abundant, red flowers and attractive foliage. This new and distinct variety has shown to be uniform and stable in the resulting generations from asexual propagation.

2 Drawing Sheets

Botanical designation: *Rosa hybrida.*
Variety denomination: 'Poulpah106'.

This application claims priority to Plant Breeder's Rights Application Number 2020/2249, which was filed at the Community Plant Variety Rights Office in the European Union on Sep. 21, 2020, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulpah106', originated as a single seedling from the stated cross.

The new variety may be distinguished from its male pollen parent and female seed parent primarily by the following characteristics. The male pollen parent plant has light pink flowers while the new variety has red flowers. The female seed parent plant has deep pink flowers while the new variety has red flowers.

The objective of the hybridization of this rose variety was to create a new and distinct variety with unique qualities, such as:

1. Uniform and abundant red flowers;
2. Vigorous, but compact growth when propagated on its own roots;
3. Exceptional disease resistance.

This combination of qualities is not present in previously available commercial cultivars of this type, known to the inventor, and distinguish 'Poulpah106' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulpah106' was selected in the spring of 2011 by the inventor as a single plant from the progeny of the aforementioned hybridization.

Asexual reproduction of 'Poulpah106' by rooted cuttings was first done by Mogens N. Olesen in the nursery in Fredensborg, Denmark in July, 2011. This initial and other subsequent asexual propagations conducted in controlled environments have demonstrated that the characteristics of 'Poulpah106' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah106'.

Specifically illustrated in FIG. 1 of the drawings are flower buds, open flowers viewed from above and side as well as with petals detached, showing reproductive parts, sepals, receptacle, and pedicel.

Figure 1:
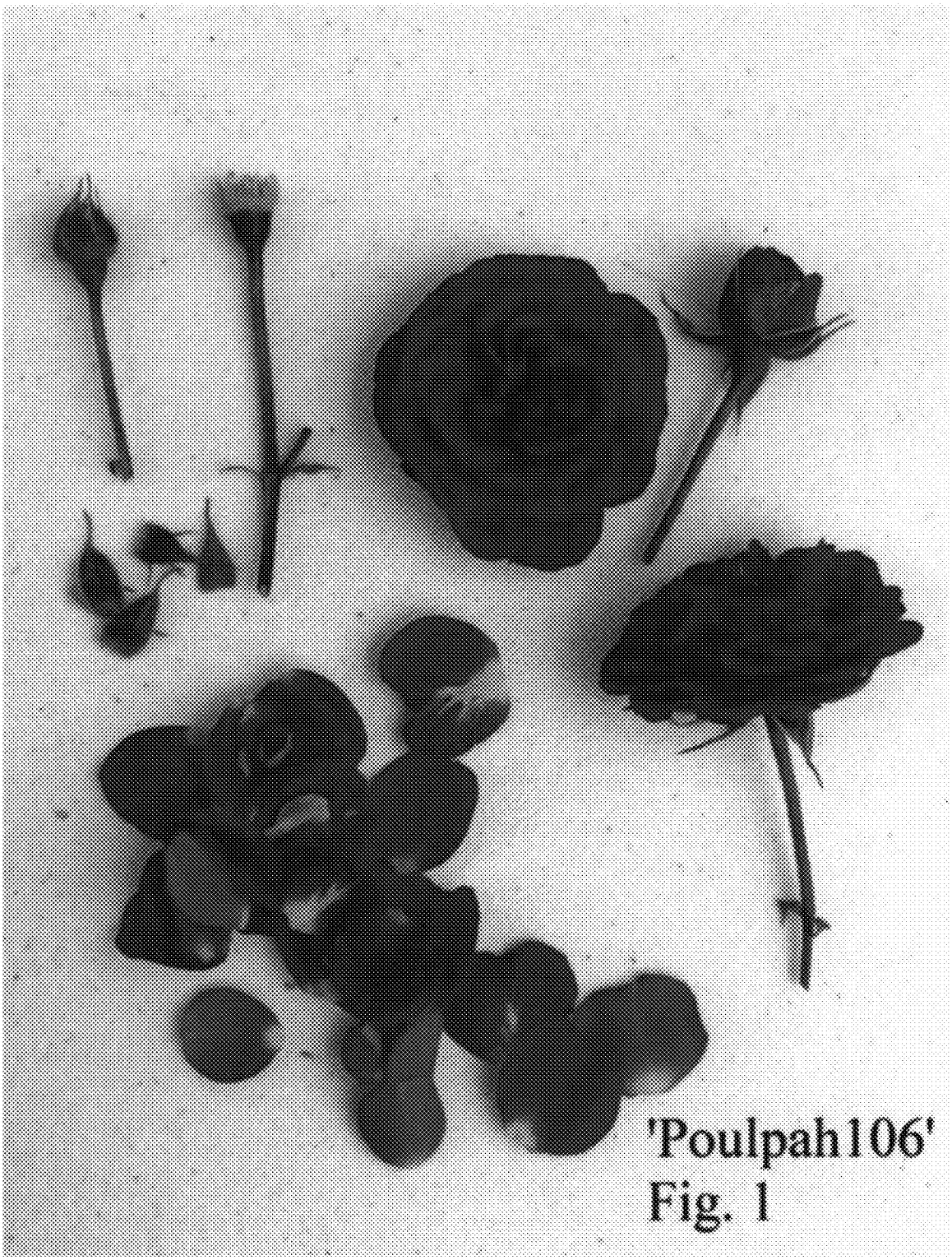
Figure 2:
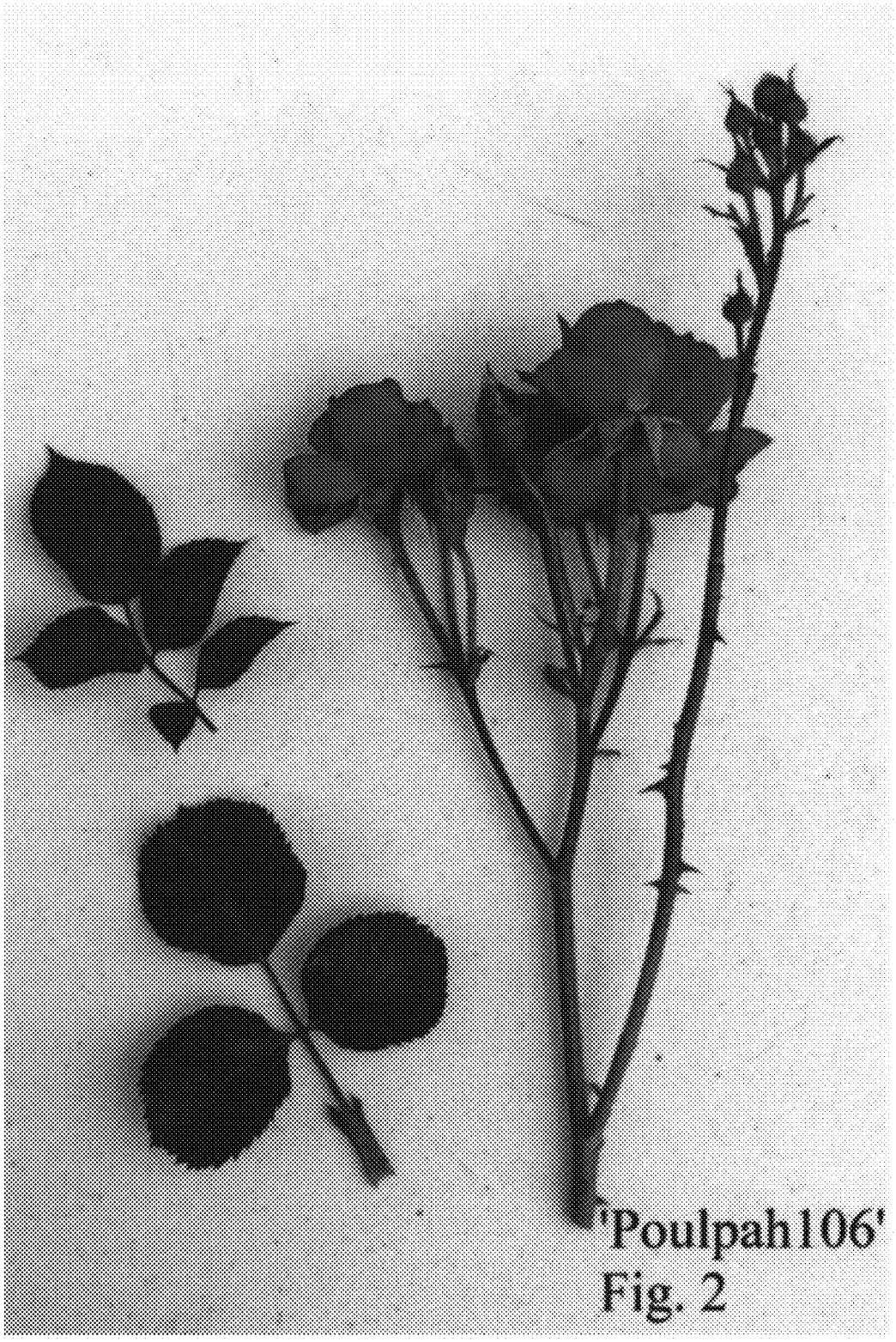

Specifically illustrated in FIG. 2 of the drawings is a cluster of open flowers on the branch, leaves, and bare stem. Plants shown are 2 years of age.

DETAILED DESCRIPTION OF THE VARIETY

The following is a description of 'Poulpah106', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpah071', U.S. Plant Pat. No. 27,024 are compared to 'Poulpah106' in Chart 1.

CHART 1

| | 'Poulpah106' | 'Poulpah071' |
|---|---|---|
| Petal Count | 50 | 40 |
| Flower Diameter | 67 | 50 mm |
| General Tonality of Flower Color | Red Group 53B | Red-Purple Group 46B |

FLOWER AND FLOWER BUD

Blooming habit: Continuous.

Flower bud:

*Size*.—Upon opening, 20 mm in length from base of receptacle to end of bud. Bud diameter is 19 mm.

*Bud form*.—Urceolate.

*Bud color*.—As sepals divide petals are Red Group 53B.

*Sepal inner surface*.—Color: Yellow-Green Group 145C with intonations of Greyed-Purple Group 185C. Surface: Lightly pubescent.

*Sepal outer surface*.—Color: Yellow-Green Group 144A with intonations of Greyed-Purple Group 185B. Texture: Many stipitate glands.

*Sepal shape*.—Generally subulate. Apex: Cirrhose. Base: Flat at union with receptacle.

*Sepal margin*.—Margins have weak foliaceous appendages on three of the five sepals.

*Sepal size*.—22 mm long, 9 mm wide.

*Receptacle*.—Texture: Smooth. Size: 8 mm in height, 8 mm wide. Color: Yellow-Green Group 144A with intonations of Greyed-Purple Group 183B. Shape: Campanulate.

*Pedicel*.—Surface: Smooth. Length: 45 mm. Diameter: 2 mm on average. Color: Yellow-Green Group 144A with intonations of Greyed-Purple Group 183C. Strength: Strong.

*Peduncle*.—Length: 3 to 7 cm. Diameter: About 3 mm. Color: Yellow-Green Group 144A with Greyed-Purple Group 183C. Texture: Smooth.

Flower bud development: Flower buds are borne in panicles consisting of clusters of 3 to 9 flower buds per stem.

Flower bloom:

*Fragrance*.—Moderate.

*Duration*.—The blooms have a duration on the plant of approximately 12 days. Petals fall cleanly away from plant after flowers have fully matured.

*Size*.—Flower diameter is 67 mm when open. Flower depth is 23 mm.

*Flower shape*.—Shallow cup.

*Shape of flower, side view*.—The upper portion is convex. The lower portion is concave.

Petalage: Under normal conditions, flowers have about 50 petals.

General tonality of flower: Open flowers are Red Group 53B.

Petal color:

*Outer petals*.—Upper surface: Red Group 46B with intonations of Red 53A. Lower surface: Red Group 53C with occasional streaks of White Group 155C on the guard petals.

*Inner petals*.—Upper surface: Red Group 53B. Lower surface: Red-Purple Group 58B splashed with Red-Purple Group 62C.

*Basal petal spots*.—Upper surface: Yellow Group 4A. Lower surface: Yellow Group 4C.

Petals:

*Petal reflex*.—Not reflexed.

*Margin*.—Entire and uniform. None or slight undulations.

*Shape*.—Broad and elliptic. Apex shape: Rounded occasionally emarginate. Base shape: Acute.

*Size*.—30 mm (l)×35 mm (w).

*Texture*.—Smooth.

*Thickness*.—Average.

Petaloids:

*Size*.—9 mm (l) by 6 mm (w).

*Quantity*.—About 6.

*Shape*.—Elliptical with an acute base and rounded apex.

*Color*.—Red Group 53B on the upper surface, with Red-Purple Group 58B on the lower surface. Petal spot is Green-White Group 157A and Yellow Group 4C.

Reproductive flower parts:

*Pollen*.—None observed.

*Anthers*.—Size: 2 mm in length. Color: Yellow-Orange Group 14A and Yellow Group 11C. Quantity: 38 on average.

*Filaments*.—Color: Yellow Group 8A. Length: 8 mm.

*Pistils*.—Length: 6 mm. Quantity: 23 on average.

*Stigmas*.—Color: Green-White Group 157A.

*Styles*.—Color: Green-White Group 157A.

*Location of stigmas*.—Inferior in location relative to the length of the filaments and the height of the anthers.

*Hips*.—None Observed.

PLANT

Plant growth: Compact, upright and well branched. Plants are 42 cm in height, and 38 cm wide.

Stems:

*Color of juvenile growth*.—Yellow-Green Group 144A with intonations of Greyed-Purple Group 184A.

*Color of mature growth*.—Yellow-Green Group 146B.

*Length*.—Canes are about 15 cm from the base of the plant to the flowering portion.

*Diameter*.—About 5 mm.

*Internodes*.—On mature canes about 50 mm between nodes.

*Surface texture*.—Young wood: Smooth. Older wood: Smooth.

Long prickles:

*Incidence*.—5 prickles per 10 cm of stem.

*Size*.—Average length of prickles on mature stems is 8 mm.

*Shape*.—Upper portion is linear. Lower portion is concave.

*Color*.—Juvenile prickles: Greyed-Red Group 179A. Mature prickles: Greyed-Yellow Group 160A with intonations of Greyed-Red Group 178B.

Plant foliage:

*Compound leaf*.—115 mm (l)×80 mm (w).

*Quantity*.—2 leaves per 10 cm of stem on average.

*Leaf bearing angle to the stem*.—45 degrees.

*Color of juvenile foliage*.—Upper side: Yellow-Green Group 146B with intonations of Greyed-Red Group 178A at the margins. Lower side: Yellow-Green Group 146B shaded with Greyed-Red Group 178A.

*Color of mature foliage*.—Upper side: Yellow-Green Group 147A. Lower side: Yellow-Green Group 147C.

Plant leaves and leaflets:

*Stipules*.—Size: 22 mm long, 3 or 4 mm wide. Quantity: 2 per compound leaf. Shape: Linear, slightly broad based with outward extending apices. Margins: Finely serrated. Color: Yellow-Green Group 144A with light intonations of Greyed-Purple Group 184C.

*Petiole*.—Length: 25 mm. Diameter: 2 mm. Upper surface color: Yellow-Green Group 144A with intonations of Greyed-Purple Group 184A. Lower surface color: Yellow-Green Group 144A.

*Rachis*.—Length: 30 to 40 mm. Diameter: About 1.5 mm. Upper surface color: Yellow-Green Group 144A with intonations of Greyed-Purple Group 184A. Lower surface color: Yellow-Green Group 144A.

*Leaflet*.—Quantity: Normally 5 leaflets. Occasionally leaves are trifoliate. Margins: Serrated. Size: Terminal leaflets are about 45 mm long, 42 mm wide. Shape: Generally orbicular. Base: Rounded. Apex: Mucronate. Texture: Smooth. Thickness: Above average. Arrangement: Odd pinnate. Venation: Reticulate. Glossiness: Very glossy.

Disease resistance: Above average resistance to powdery mildew *Sphaerotheca pannosa* var. *rosae,* downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

Pest resistance: The variety is susceptible to any insect pest normally associated with the species.

I claim:

1. A new and distinct variety of rose plant of the Miniature rose class named 'Poulpah106', substantially as illustrated and described herein, due to its abundant red flowers, disease resistance, and extended period of bloom.

* * * * *

'Poulpah106'

'Poulpah106'